US010251908B2

(12) United States Patent
Feller et al.

(10) Patent No.: US 10,251,908 B2
(45) Date of Patent: *Apr. 9, 2019

(54) VITAMIN B$_{12}$ NASAL SPRAY AND METHOD OF USE

(71) Applicants: PAR PHARMACEUTICAL, INC., Chestnut Ridge, NY (US); Patrick J. Arnall, St. Louis, MO (US)

(72) Inventors: Theodore H. Feller, St. Louis, MO (US); Angela Sutterer, St. Louis, MO (US); Thomas E. Fleming, St. Louis, MO (US)

(73) Assignee: ENDO PHARMACEUTICALS INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/738,417

(22) Filed: Jun. 12, 2015

(65) Prior Publication Data
US 2015/0272876 A1  Oct. 1, 2015

Related U.S. Application Data

(63) Continuation of application No. 12/618,099, filed on Nov. 13, 2009, now Pat. No. 9,186,374, which is a continuation of application No. 11/506,148, filed on Aug. 17, 2006, now abandoned.

(60) Provisional application No. 60/709,200, filed on Aug. 17, 2005.

(51) Int. Cl.
| *A61K 31/714* | (2006.01) |
| *A61K 9/00* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61M 11/00* | (2006.01) |
| *A61M 15/08* | (2006.01) |

(52) U.S. Cl.
CPC .......... *A61K 31/714* (2013.01); *A61K 9/0043* (2013.01); *A61K 47/02* (2013.01); *A61K 47/10* (2013.01); *A61K 47/12* (2013.01); *A61K 47/186* (2013.01); *A61M 11/006* (2014.02); *A61M 15/08* (2013.01)

(58) Field of Classification Search
CPC ..... A61K 31/714; A61K 47/02; A61K 9/0043
See application file for complete search history.

(56) References Cited

U.S. PATENT DOCUMENTS

| 2,703,302 A | 3/1955 | Rickes et al. |
| 2,703,303 A | 3/1955 | Rickes et al. |
| 2,746,796 A | 5/1956 | Germain et al. |
| 2,914,222 A | 11/1959 | Meshberg |
| 2,951,017 A | 8/1960 | Speedie et al. |
| 3,000,793 A | 9/1961 | McDaniel |
| 3,018,225 A | 1/1962 | Long |
| 3,057,851 A | 10/1962 | Van Melle |
| 3,120,508 A | 2/1964 | Braun et al. |
| 3,120,509 A | 2/1964 | Bernhauer et al. |
| 3,282,781 A | 11/1966 | Macck et al. |
| 3,547,138 A | 12/1970 | Kelley et al. |
| 3,577,537 A | 5/1971 | Howe et al. |
| 3,584,115 A | 6/1971 | Gebhart et al. |
| 3,957,968 A | 5/1976 | Cordon |
| 4,174,295 A | 11/1979 | Bargigia et al. |
| 4,523,341 A | 6/1985 | Queen |
| 4,525,341 A | 6/1985 | Deihl |
| 4,724,231 A | 2/1988 | Wenig |
| 4,727,231 A | 2/1988 | Hayano et al. |
| 4,782,047 A | 11/1988 | Benjamin et al. |
| 4,959,176 A | 9/1990 | Slocum et al. |
| 5,112,804 A | 5/1992 | Kowarski |
| 5,277,311 A | 1/1994 | Hollister |
| 5,797,390 A | 8/1998 | McSoley |
| 5,801,161 A | 9/1998 | Merkus |
| 5,825,625 A | 10/1998 | Esterberg et al. |
| 5,925,625 A | 7/1999 | Merkus |
| 6,166,025 A | 12/2000 | Harding et al. |
| 6,406,730 B1 | 6/2002 | Banyard et al. |
| 6,665,421 B1 | 12/2003 | Farina |

(Continued)

FOREIGN PATENT DOCUMENTS

| CA | 1317881 | 5/1993 |
| EP | 0131315 A2 | 2/1984 |

(Continued)

OTHER PUBLICATIONS

Fageria et al., Commun. Soil Sci. Plant. Anal., 2012, 43, p. 556-570.*
Ahmad et al., J. Pharm. Biomed. Anal., 1992, 10(1), p. 9-15.
Allen, 2002, "Prescription," Intl. J. Pharmaceutical Compounding, vol. 6(3): 208.
Bartilucci et al., J. Am. Pharm. Assoc., 1958, 43(3), p. 159-162.
Bean. Journal of the Society of Cosmetic Chemists, 23 (1972), 703-720.
Behl et al. Advanced Drug Delivery Reviews, 29 (1998): 89-116.
Braat et al., Clinical and Experimental Allergy, 25 (1995): 957-965.
Chandra et al, 1982, "Double-blind controlled crossover trial of 4% intranasal sodium crymoglycate solution in patients with seasonal allergic rhinitis," Annals of Allergy, vol. 49, from the Dept. of Pediatrics, Memorial University of Newfoundland, Janeway Child Health Center and Health Sciences Center. St. John's Newfoundland, Canada.

(Continued)

Primary Examiner — Jonathan S Lau
(74) Attorney, Agent, or Firm — Arent Fox LLP

(57) ABSTRACT

The present invention relates generally to vitamin B$_{12}$ nasal spray compositions and methods of using the same in the treatment of vitamin B$_{12}$ deficiency and various disorders that are related to such deficiency. In particular embodiments, the present invention is directed to treatment methods comprising intranasal administration of a cobalamin composition according to a particular dosing and frequency schedule and to a preservative-free nasal spray composition comprising a cobalamin compound useful in the practice of such treatment methods.

13 Claims, 1 Drawing Sheet

(56) References Cited

U.S. PATENT DOCUMENTS

| | | |
|---|---|---|
| 6,685,421 B1 | 2/2004 | Reeves |
| 6,745,760 B2 | 6/2004 | Grychowski et al. |
| 6,911,434 B2 | 6/2005 | Baldridge et al. |
| 7,404,489 B1 * | 7/2008 | Quay ............... A61K 9/0043 206/569 |
| 2003/0018416 A1 | 1/2003 | Farina et al. |
| 2004/0034042 A1 | 2/2004 | Tsuji et al. |
| 2004/0043043 A1 | 3/2004 | Schlyter et al. |
| 2004/0109826 A1 | 6/2004 | Malladi et al. |
| 2006/0046969 A1 | 3/2006 | Maggio |
| 2006/0074034 A1 | 4/2006 | Collins et al. |
| 2006/0105432 A1 | 5/2006 | Barg et al. |
| 2006/0127320 A1 | 6/2006 | Costantino et al. |

FOREIGN PATENT DOCUMENTS

| | | |
|---|---|---|
| EP | 0130550 A2 | 6/1984 |
| JP | S62-283927 A | 12/1987 |
| JP | H03-129153 | 12/1991 |
| JP | H05-170663 A | 7/1993 |
| JP | 200-516262 A | 12/2000 |
| JP | 2003-038940 A | 2/2003 |
| WO | WO 86/05987 | 10/1986 |
| WO | WO 86/05988 | 10/1986 |
| WO | WO 99/01135 A1 | 1/1999 |
| WO | WO 00/33810 | 6/2000 |
| WO | WO 01/13092 A1 | 2/2001 |
| WO | WO 01/13322 A1 | 2/2001 |
| WO | WO 2005/004895 A2 | 1/2005 |
| WO | WO 07/022345 | 2/2007 |

OTHER PUBLICATIONS

Cutie et al.. 1982, "Intranasal pharmaceutical aerosols, aerosal age. the international authority in spray packaging," Aerosol Age Magazine, Oct. 1982. pp. 1-4.
Edited by James E.F, Reynolds, Cyanocobalamin, Martindale, The Extra Pharmacopoeia, 1982, Abstract 7853-d. and p. 1645. Cyanocobalamin Injection, 28111 Edition. Published by direction of the Council of The Pharmaceutical Society of Great Britain and prepared in the Society's Dept. of Pharmaceutical Sciences, The Pharmaceutical Press, London, UK.
England et al., Clin. Otolaryngol., 1999, p. 67-68.
FDA Guidance for Industry on Container Closure Systems for Packing Human Drugs and Biologics, May 1999.
Forest Laboratories, Inc., 1972 "Long acting oral carrier," Chemical Abstracts, vol. 77, p. 263. Abstract 105623(y).
Garcia-Arieta et al., 2001,"Spray-dried powders as nasal absorption enhancers of cyanocobalamin," Biol. Pharm. Bull., vol. 24(2):141 1-1416.
Harris et al., 1988. "Effect of viscosity on particle size, deposition, and clearance of nasal delivery systems containing desmopressin," J. Pharm Sci.. vol. 77(5):405-408.
Hussain et al., 1984, "Studies on the intranasal absorption of Vitamin B12 in the rat," Final Report, Dec. 1984, University of Kentucky, College of Pharmacy, Lexington, KY.
Killander et al., 1961, "Studies on maintenance treatment of pernicious anaemia, Vitamin 1112 and instrinsic factor," Europaisches Symposian Hamburg, pp. 663-687, Ed. H.c. Heinrich, Enke, Stuttgart, Dept. of Pediatris and Internal Medicine, Akademiska. Sjukhuset, Uppsala, Sweden.
Kublik, et al., Adv. Drug Deily. Rev., 1998, 29, p. 157-177.
Mathison et al., 1998, "Nasal route for direct delivery of solutes to the central nervous system: Fact or fiction?" J. of Drug Targeting, vol. 5(6):415-441.
Monto et al., 1953, "Crystalline B12 inhaliation therapy in pernicious anemia," The American Journal of the Medical Sciences, vol. 2. pp. 113-119, Publisher, Division of Hematology and Department of Laboratories, The Henry Ford Hospital, Detroit. Michigan.
Monto et al., 1954, Nasal instillation and inhalation of crystalline Vitamin B12 in pernicious anemia,—A.M.A. Archives 6 Internal Medicine, vol. 93:219-230, Division of Hematology (Dr. Monto) and the Dept of Laboratories (Dr. Rebuk), The Henry Ford Hospital.
Monto et al., 1955. "Observations on the mechanism of intranasal absorption of Vitamin B12 in pernicious anemia," Blood, vol. 10:1151-1155.
Nijst et al., 1990, "Vitamin e'2 and folate concentrations in serum and cerebrospinal fluid of neurological patients with special reference to multiple sclerosis and dementia." J. of Neurology. Neurosurgey and Psychiatry, vol. 53:951-954.
Pharmaceuticals Agent Additive Biographical Dictionary, Yakuji Nippo Limited, First Edition, p. 355 (1994).
Sciarra, J.J. Aerosols, Chapter 92, year unknown. pp. 1614-1621, Arnold & Marie Schwartz, Collet of Pharmacy and Health Sciences, Long Island University, Brooklyn, NY.
Shinton et al., 1967. "Vitamin B'2 absorption by inhalation," Brit J. Haematol., vol. 13:75-79.
Shinton et al., 1967. "Vitamin B'2 absorption by inhalation," Chemical Abstracts. vol. 66, No. 15, Coden: Chaba8, The American Chemical Society, p. 6024. Abstract 64246(2).
Slot et al., 1997, "Normalization of plasma vitamin B12 concentration by intranasal hydroxocohaiamin in Vitamin 212-defient patients." Gastro, vol. 113:430-433.
Translation of Japanese Office Action issued in Japanese Application No. 2009-516468.
Trissel, L.A., Handbook on Injectable Drugs, 2005, American Society of Health-System Pharmacists, Inc. 13th edition, p. 408-410.
U.S. Department of Health and Human Services, (Draft) 2003. "Guidance for Industry, Bioavailability and Bioequivalenee Studies for Nasal Aerosols and Nasal Sprays for Local Action." Apr. 2003. pp. 1-36 + attachments, U.S. FDA. Center for Drug Evaluation and Research. Biopharmaceutics.
U.S. Dept. of Health and Humans Services. 2002. "Guidance for Industry, Nasal spray and inhalation solution, suspension, and spray drug products—chemistry, manufacturing, and controls documentation," Jul. 2002, pp. 1-44, FDA, Center for Drug Evaluation and Research.
Valois, "Pumps for Pharmacy," Year unknown (product brochure).
Washington et al. International Journal of Pharmaceutics, 198 (2000) 139-146.
Watanabe et al., "Na-CMC and use thereof", Production Research, vol. 12, No. 5, right column, lines 14 to 20, p. 219 (1960).
Yu et al.. 1983, Characterization of dose delivery and spray pattern of a metered-dose flunisolide nasal spray, Drug development and industrial pharmacy, vol. 9(3):473-483. Institute of Pharmaceutical Sciences, Syntex Research, Palo Alto, CA Mercel Dekker. Inc.

* cited by examiner

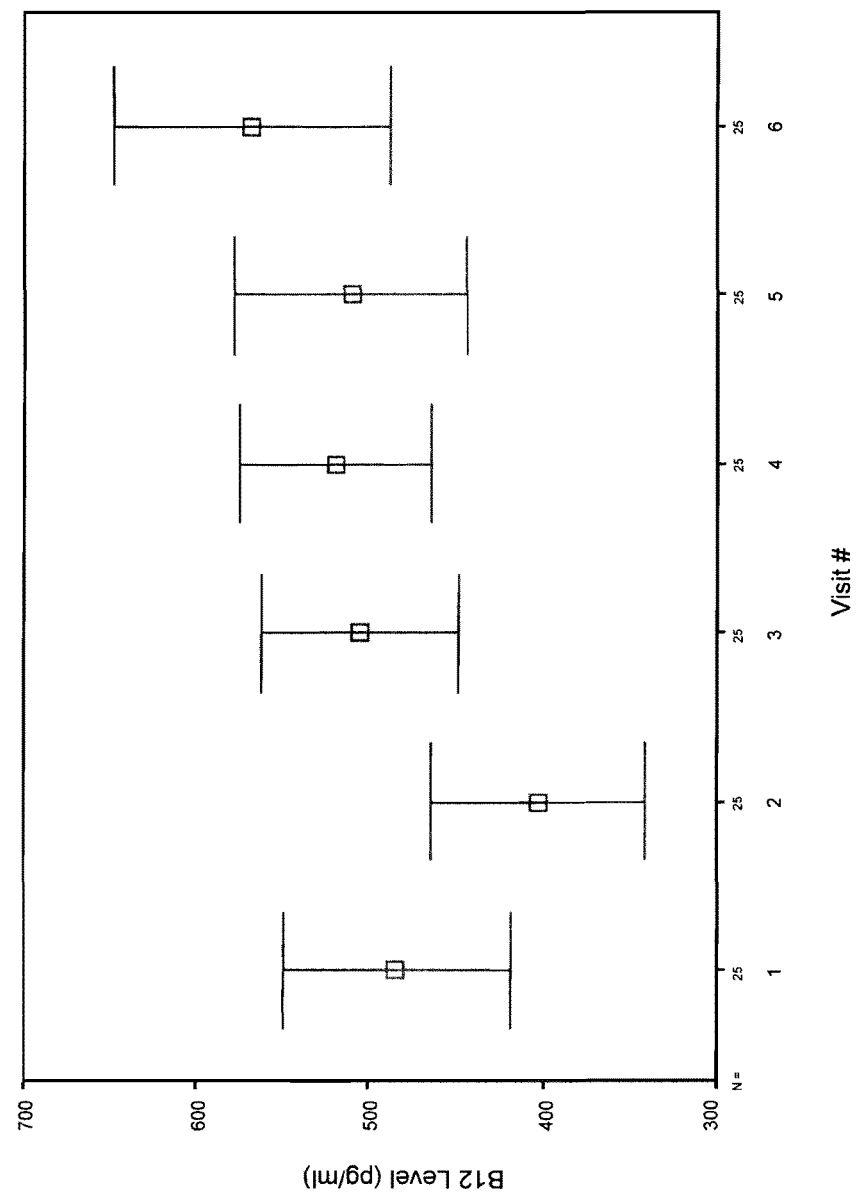

VITAMIN $B_{12}$ NASAL SPRAY AND METHOD OF USE

CROSS-REFERENCE TO RELATED APPLICATION

This application is a Continuation of U.S. patent application Ser. No.: 12/618,099, filed Nov. 13, 2009, which is a Continuation of U.S. patent application Ser. No.: 11/506,148, filed Aug. 17, 2006; which claims the benefit of priority to U.S. Provisional Application No. 60/709,200, filed Aug. 17, 2005. The disclosures of the prior applications are hereby incorporated in their entirety by reference.

FIELD OF THE INVENTION

The present invention relates generally to vitamin $B_{12}$ nasal spray compositions and methods of using the same in the treatment of vitamin $B_{12}$ deficiency and various disorders that are related to such deficiency. In particular embodiments, the present invention is directed to treatment methods comprising intranasal administration of a cobalamin composition according to a particular dosing and frequency schedule and to a preservative-free nasal spray composition comprising a cobalamin compound useful in the practice of such treatment methods.

BACKGROUND

Vitamin $B_{12}$ is a water soluble vitamin that plays a role in mammalian growth, hematopoiesis, production of epithelial cells, and maintenance of the nervous system. It was first isolated from liver concentrate in 1948 and structurally elucidated in the late 1950's.

Cyanocobalamin is a form of vitamin $B_{12}$ and is one of the class of $B_{12}$ vitamins or cobalamin compounds that includes vitamin $B_{12a}$ (hydroxocobalamin), vitamin $B_{12b}$ (aquacobalamin), vitamin $B_{12c}$ (nitrilocobalamin), methyl $B_{12}$ (methylcobalamin) and coenzyme $B_{12}$ (5'deoxyadenosine cobalamin). Cyanocobalamin and hydroxocobalamin are the principal members of the class and the most widely employed in compositions used to treat vitamin $B_{12}$ deficiency and disorders that are related to this deficiency. Such disorders include anemias (most commonly pernicious anemia) and *diphyllobothrium latum* (fish tapeworm) infestation of the intestine, a disorder with symptomology that mimics pernicious anemia.

Several routes of administration of vitamin $B_{12}$ are known. Among these are parenterally, including intramuscular and subcutaneous injection, orally as a component of a tablet or solution, and nasally, as a component of a nasal spray or gel. Although the minimum daily dietary requirement of vitamin $B_{12}$ is approximately 0.1 µg for a healthy human, therapeutic administration of vitamin $B_{12}$ is typically in significantly larger doses. For example, the prescribed initial therapeutic dose is generally from about 100 µg to about 1000 µg, and is most often administered by intramuscular injection. Subsequent vitamin $B_{12}$ maintenance therapy may be by injection or by oral administration of a cobalamin composition. Use of vitamin $B_{12}$ injections for maintenance therapy has obvious disadvantages, including the inconvenience and pain associated with the injection that typically must be administered by medical personnel. Orally administered cobalamin compositions may fail to be adequately absorbed in the patient, particularly in those in which secretion or utilization of intrinsic factor is inadequate.

Intranasal administration of cobalamin compositions for vitamin $B_{12}$ maintenance therapy offers advantages over these alternative routes of administration. Typically, such therapy includes relatively infrequent, high dose nasal administration of a cobalamin composition. For example, NASCOBAL nasal spray solution containing 0.5% by weight cyanocobalamin is administered in one nostril once weekly in a dose of 500 µg (i.e., 500 µg cyanocobalamin per 0.1 mL actuation of the spray bottle pump).

Although maintenance therapy with vitamin $B_{12}$ nasal compositions has proven generally effective, those undergoing such therapy may experience some irritation of the nasal mucosa and discomfort due, in part, to the high dosage of the cobalamin compound typically administered as well as preservatives and other additives often present in these compositions. Moreover, effective vitamin $B_{12}$ maintenance therapy would be enhanced if more stable or even blood serum levels of vitamin $B_{12}$ could be attained through intranasal administration of a cobalamin composition. Accordingly, a need persists for improvements in vitamin $B_{12}$ nasal compositions and methods of nasal administration of such compositions in the treatment of vitamin $B_{12}$ deficiency and various vitamin $B_{12}$ deficiency-mediated disorders.

SUMMARY OF THE INVENTION

Among the various aspects of the present invention is the provision of a method of frequent, low dose nasal administration of a vitamin $B_{12}$ composition and an improved vitamin $B_{12}$ composition suitable for use in such methods of treatment.

Briefly, therefore, the present invention is directed to a method for maintaining vitamin $B_{12}$ blood serum levels in a mammals, the method comprising nasally administering to the mammal at least once every three days an aqueous composition comprising a cobalamin compound in an amount sufficient to deliver a dose of no more than about 150 µg of the cobalamin compound to the mammal.

The present invention is further directed to a method for maintaining normal hematologic status in a pernicious anemia patient following intramuscular vitamin $B_{12}$ injection therapy, the method comprising nasally administering to said patient at least once every three days an aqueous composition comprising a cobalamin compound in an amount sufficient to deliver a dose of no more than about 150 µg of the cobalamin compound to the patient.

The present invention is further directed to a composition for nasal administration of a cobalamin compound, the composition comprising an aqueous solution containing a cobalamin compound and a pharmaceutically acceptable buffer, the composition having a pH of at least about 6.5.

The present invention is further directed to a composition for nasal administration of a cobalamin compound, the composition comprising an aqueous solution containing a cobalamin compound and a pharmaceutically acceptable buffer and being free of preservatives.

Other objects and features will be in part apparent and in part pointed out hereinafter.

BRIEF DESCRIPTION OF THE DRAWINGS

FIG. 1 depicts the mean serum vitamin $B_{12}$ levels and 95% confidence interval for all six visits in the study conducted in the Example.

DETAILED DESCRIPTION OF THE INVENTION

The present invention is based in part on the observation that conventional intranasal administration of cobalamin compositions may lead to irritation of the nasal membranes or mucosa. Irritation may be caused or exacerbated by the relatively high dose of cobalamin compound typically administered and/or preservatives and other additives commonly contained in these compositions. This irritation, compounded by infrequent, high dose administration of conventional intranasal cobalamin compositions (e.g., anywhere from once a week to as rarely as once a month), can lead to patient noncompliance and variable blood serum vitamin $B_{12}$ levels and ultimately to inconsistent or ineffective treatment of vitamin $B_{12}$ deficiency-mediated disorders.

In order to provide patients with a more consistent and effective treatment for vitamin $B_{12}$ deficiency and related disorders, the present invention is directed to methods for maintaining vitamin $B_{12}$ blood serum levels in a mammal comprising more frequent intranasal administration of a cobalamin composition and at lower dosages than previously recognized as effective in the treatment of such disorders. The present invention further provides compositions containing a cobalamin compound useful in the practice of the treatment methods disclosed herein, while minimizing the risk of irritation of the nasal mucosa and patient noncompliance with the prescribed treatment regimen.

The treatment methods disclosed herein are generally applicable for maintenance of vitamin $B_{12}$ blood serum levels in a patient in need of vitamin $B_{12}$ therapy. Such a patient may be suffering from a vitamin $B_{12}$ deficiency, a disorder resulting from such a deficiency, or a disorder mimicking the symptomology of such a deficiency. Examples of disorders resulting from or mimicking a vitamin $B_{12}$ deficiency include, for example, anemia, including pernicious anemia; nerve degeneration, typically as a result of degradation or lack of myelin; and infestation by intestinal parasites or bacteria such as *diphyllobothrium latum* (fish tapeworm) that absorb large quantities of vitamin $B_{12}$ in the host. Other indications for application of the treatment methods disclosed herein include, for example, maintenance of normal hematologic status in pernicious anemia patients in remission subsequent to intramuscular vitamin $B_{12}$ injection therapy and who have no nervous system involvement; remedying vitamin $B_{12}$ dietary deficiencies (e.g., in vegetarians); treatment of patients suffering from vitamin $B_{12}$ malabsorption phenomena such as that resulting from inadequate secretion and/or utilization of intrinsic factor (e.g., due to HIV infection, AIDS, Crohn's disease, tropical and nontropical sprue, extensive neoplasia, subtotal or total gastrectomy, etc.); maintenance of vitamin $B_{12}$ in excess of normal dietary requirements due to pregnancy, renal disease, thyrotoxicosis, hemolytic anemia, hemorrhage, etc; and patients having elevated serum homocysteine, cystathionine, methylmalonic acid and/or 2-methylcitric acid levels.

The present invention is directed particularly to the treatment of humans in need of vitamin $B_{12}$ therapy. However, it should be understood that the methods disclosed herein are generally applicable to the treatment of mammals including, for example, domesticated house pets, such as dogs and cats, as well as farm animals, such as cattle, pigs, horses, sheep and goats.

Methods for Intranasal Administration of a Cobalamin Containing Composition

Generally, the treatment methods of the present invention comprise more frequent and lower dose intranasal administration of a composition containing a cobalamin compound. It has been discovered that more frequent and lower dose intranasal administration of a cobalamin composition offers several advantages over conventional intranasal vitamin $B_{12}$ maintenance therapy, including reduced risk of irritation of the nasal mucosa and more stable or even vitamin $B_{12}$ blood serum levels (i.e., smaller peak to trough variances) by more closely mimicking the typical mammalian dietary intake of vitamin $B_{12}$. Moreover, it is believed that patient compliance is improved by treatment regimens including more frequent administration of the cobalamin composition. As described in greater detail below, the compositions used in the practice of the methods disclosed herein include, for example, aqueous solutions of the cobalamin compound along with various optional components such as isotonicity agents, buffering agents, humectants, surfactants and preservatives.

The treatment method for maintaining vitamin $B_{12}$ blood serum levels in a mammal in accordance with the present invention comprises nasally administering to the mammal an aqueous composition comprising a cobalamin compound at least once every three days, preferably at least once every two days. The frequency of administration may vary during the treatment period. For example, the composition may be administered every day during an initial portion (e.g., the first week or first two weeks) of the treatment period (e.g., daily during an initial "loading" period to increase vitamin $B_{12}$ blood serum levels), and then at less frequent intervals during the remainder of the treatment period. However, in order to promote patient compliance, administration preferably occurs at regular intervals throughout the treatment period. In accordance with a more preferred embodiment, the treatment method of the present invention comprises daily intranasal administration (i.e., one or more administrations per day), and especially once daily, intranasal administration of the cobalamin composition during the treatment period.

The dose of the cobalamin compound delivered to the patient with each administration will vary generally with the frequency of administration (a higher dose being utilized with longer intervals between administrations), as well as with the needs of the patient and the type of disorder being treated, as would be apparent to those skilled in the art, but is generally lower than the dosing conventionally employed. Generally, the dose of the cobalamin compound delivered to the patient with each administration is no more than about 150 μg, preferably no more than about 125 μg, more preferably no more than about 100 μg, and still more preferably no more than about 75 μg of the cobalamin compound, and is at least 5 μg, preferably at least about 10 μg of the cobalamin compound.

With respect to a preferred treatment regimen comprising daily intranasal administration of a cobalamin composition, the daily dose of the cobalamin compound delivered to the patient is preferably from about 5 μg to about 100 μg, more preferably from about 20 μg to about 80 μg, still more preferably from about 30 μg to about 70 μg and even more preferably from about 40 μg to about 60 μg. In accordance with an especially preferred embodiment comprising once daily intranasal administration of the cobalamin composition, the dose of the cobalamin compound delivered to the patient with each administration is usually no more than about 80 μg. In such an embodiment, the dose of the cobalamin compound delivered to the patient with each administration is preferably from about 5 μg to about 80 μg, more preferably from about 10 μg to about 60 μg, more preferably from about 15 μg to about 50 μg, more preferably from about 20 μg to about 50 μg, more preferably from about 30 µg to about 50 µg, still more preferably from about 40 µg to about 50 µg and even more preferably from about 45 µg to about 50 µg. For example, in an embodiment comprising daily intranasal administration of the cobalamin composition, the dose of the cobalamin compound delivered to the patient per administration may be about 10 µg, about 15 µg, about 20 µg, about 25 µg, about 30 µg, about 35 µg, about 40 µg, about 45 µg, or about 50 µg.

In accordance with another embodiment of the treatment method disclosed herein comprising once daily intranasal administration of the cobalamin composition, the dose of the cobalamin compound delivered to the patient with each administration is from about 5 µg to about 45 µg, preferably from about 10 µg to about 45 µg, more preferably from about 15 µg to about 45 µg, more preferably from about 20 lag to about 45 µg, still more preferably from about 30 µg to about 45 µg, and even more preferably from about 40 µg to about 45 µg.

With respect to the dose of the cobalamin compound delivered to the patient per administration, it should be understood that each administration may comprise one or a plurality of applications or sprays of the cobalamin composition delivered to the nasal mucosa of the patient through one or both nostrils, the number of applications or sprays being dependent upon the concentration of the cobalamin compound in the composition, the quantity of the composition delivered per spray, and the desired dose per administration as readily determined by one skilled in the art. As described in greater detail below, the cobalamin composition is preferably dispensed from a spray bottle including a pump (e.g., a manually actuated pump) capable of delivering a metered spray of the cobalamin composition of predetermined volume (typically about 0.1 mL). Furthermore, and by way of example, a daily dose of 50 µg of a cobalamin compound may be administered in a single administration comprising one or more applications or metered sprays containing a total of 50 µg of cobalamin compound (e.g., a single administration comprising two applications or metered sprays, one in each nostril and each containing 25 µg of cobalamin compound) or in multiple administrations (e.g., four administrations at six hour intervals, each administration comprising one or more applications or metered sprays, in one or both nostrils, each administration containing a total of 12.5 µg of cobalamin compound).

The weekly dose of the cobalamin compound received by the patient will generally not be in excess of about 1000 µg, more preferably about 800 µg, still more preferably about 600 µg, even more preferably about 500 µg, still more preferably about 450 µg, even more preferably about 400 µg, and most preferably not in excess of about 350 µg of the cobalamin compound. Accordingly, in one embodiment, the patient may receive a weekly dosage of from about 50 µg to about 500 µg of the cobalamin compound. In another embodiment, the patient may receive a weekly dosage of from about 100 µg to about 450 µg of the cobalamin compound. In yet another embodiment, the patient may receive a weekly dosage of from about 150 µg to about 400 µg of the cobalamin compound. In still another embodiment, the patient may receive a weekly dosage of from about 200 µg to about 400 µg of the cobalamin compound. In yet another embodiment, the patient may receive a weekly dosage of from about 250 µg to about 350 µg of the cobalamin compound. In still another embodiment, the patient may receive a weekly dosage of from about 300 µg to about 350 µg of the cobalamin compound. In a particularly preferred embodiment, the patient may receive a weekly dosage of about 350 µg of the cobalamin compound, delivered by once daily nasal administration of 50 µg of a cobalamin compound.

Compositions Containing a Cobalamin Compound

A further aspect of the present invention is a composition comprising a cobalamin compound that may be used in a regimen to treat vitamin $B_{12}$ deficiency and deficiency related disorders. The composition may be used in previously known regimens of treatment for vitamin $B_{12}$ deficiency, but preferably is used in the practice of the treatment regimen of the present invention described above.

A composition of the present invention generally comprises an aqueous solution containing a cobalamin compound. The aqueous solution is preferably isotonic. The cobalamin may be any of a number of known cobalamin compounds, including for example, cyanocobalamin, hydroxocobalamin (vitamin $B_{12a}$), hydroxocobalamin HCl, sulfate, acetate and other hydroxocobalamin salts, aquacobalamin (vitamin $B_{12b}$), nitrilocobalamin (vitamin $B_{12c}$), methylcobalamin (methyl $B_{12}$), 5'-deoxyadenosine cobalamin (coenzyme $B_{12}$), pharmaceutically acceptable salts thereof, chemically modified equivalents thereof, and mixtures thereof. The selection of the specific form of cobalamin to be used in the composition depends upon a number of factors known to those of skill in the art, including, for example, the composition in which the cobalamin compound is to be mixed or dissolved, the amount or concentration of cobalamin compound desired in the composition, the solubility of the cobalamin compound and the pH of the composition. In one embodiment, the cobalamin compound is cyanocobalamin USP. In another embodiment, the cobalamin compound is hydroxocobalamin. The concentration of the cobalamin compound in the composition can vary depending upon a number of factors known to those skilled in the art, including, for example, the composition in which the cobalamin compound is to be mixed or dissolved, the solubility of the cobalamin compound, the pH of the composition, the means by which the cobalamin composition is delivered to the nasal mucosa (e.g., using compressed gas or a propellant), the volume of the spray dispensed per application and the desired dosage to be delivered to the patient. Generally, the cobalamin compound may be present in the composition in a concentration of no more than about 20 weight percent (% w/w), for example, from about 0.0001% w/w to about 20% w/w, preferably from about 0.01% w/w to about 10% w/w, more preferably from about 0.02% w/w to about 1% w/w, still more preferably from about 0.02% w/w to about 0.04% w/w and most preferably about 0.025% w/w.

The isotonicity of the composition may generally be achieved and maintained using sodium chloride or another pharmaceutically acceptable isotonicity agent, such as, for example, dextrose, boric acid, sodium tartrate, other organic or inorganic solutes and mixtures thereof. The isotonicity agent is typically present in the composition in a concentration sufficient to cause the osmolarity of the composition to be from about 280 mOsmols to about 290 mOsmols ±50 mOsmols. Sodium chloride is generally preferred, particularly if a buffer containing sodium ions is used in the composition, and is typically present in an amount that is physiologically equivalent to the tonicity of the nasal membranes.

The cobalamin composition of the present invention may further include a pharmaceutically acceptable buffer in order to maintain the desired pH. Non-limiting examples of suitable buffers used to adjust and maintain the pH of the composition include acetate, citrate, prolamine, phosphate, carbonate, phthalate, borate, or other pharmaceutically acceptable buffers and mixtures thereof. In a particular embodiment, the buffer comprises sodium phosphate. The pH of the composition is maintained generally to be compatible with the fluids of the nasal membrane in order to minimize irritation. For example, the composition may be maintained at a pH from about 3 to about 11. In one embodiment, the composition may be maintained at a pH from about 3 to about 6.5, preferably from about 4 to about 6.5, more preferably from about 5 to about 6.5, still more preferably from about 6 to about 6.5, and most preferably about 6.5. Alternatively, the composition may be maintained at a pH greater than 6.5, preferably from about 6.5 to about 11, more preferably from about 7 to about 10, still more preferably from about 7 to about 9, even more preferably from about 7 to about 7.7, even more preferably about 7.2, and most preferably about 7.7. The concentration of the buffer in the composition will depend upon the selection of the buffer and the desired pH.

The present composition may also contain various pharmaceutically acceptable additives such as tolerance enhancers (sometimes more specifically referred to as humectants), absorption enhancers (sometimes also referred to as surfactants), preservatives, viscosity modifying agents (e.g., thickening agents), osmolarity adjusters, complexing agents, stabilizers, solubilizers, or any combination thereof.

A tolerance enhancer may be used in order to inhibit drying of the nasal membrane or mucosa. A tolerance enhancer may also serve the purpose of inhibiting or relieving irritation of the nasal membranes. Examples of suitable tolerance enhancers include, for example, humectants such as sorbitol, propylene glycol, glycerol, glycerin, hyaluronan, aloe, mineral oil, vegetable oil, soothing agents, membrane conditioners, sweeteners, and mixtures thereof. The selection and concentration of a tolerance enhancer may depend on a number of factors, including, for example, the type and concentration of cobalamin compound being used in the composition. When used, the concentration of the tolerance enhancer in the composition will typically be in amounts from about 0.01% w/w to about 20% w/w.

A surfactant or absorption enhancer may also be used in the composition in order to enhance the absorption of the cobalamin compound across the nasal membrane. Suitable absorption enhancers include non-ionic, anionic and cationic surfactants. Any of a number of well-known surfactants may be used, including, for example, polyoxyethylene derivatives of fatty acids, partial esters of sorbitol anhydrides, sodium lauryl sulfate, sodium salicylate, oleic acid, lecithin, dehydrated alcohol, Tween (e.g., Tween 20, Tween 40, Tween 60, Tween 80 and the like), Span (e.g., Span 20, Span 40, Span 80 and the like), polyoxyl 40 stearate, polyoxy ethylene 50 stearate, edetate disodium, propylene glycol, glycerol monooleate, fusieates, bile salts, octoxynol and combinations thereof. When used, the concentration of the surfactant in the composition will typically be from about 0.1% w/w to about 50% w/w. By way of example, concentrations of sodium salicylate, sodium lauryl sulfate and edetate disodium may be from about 0.01% to about 5% w/w of the composition. Concentrations of polyoxyl 40 stearate, lecithin, dehydrated alcohol, can be from about 0.1% to about 10% w/w of the composition. Concentrations of oleic acid can be from about 0.01% to about 5% w/w of the composition. Concentrations of propylene glycol and Tween 20 can be from about 0.1% to about 25% w/w of the composition.

A pharmaceutically acceptable thickening agent may also be used in the composition in order to modify the viscosity of the composition. Numerous pharmaceutically acceptable thickening agents are well-known and include, for example, methyl cellulose, xanthan gum, carboxymethyl cellulose, hydroxypropyl cellulose, carbomer, polyvinyl alcohol, alginates, *acacia*, chitosans and combinations thereof. The concentration of the thickening agent will depend upon the agent selected and the viscosity desired. Such agent may be present in the composition at a concentration of from about 0.1% w/w to about 20% w/w.

A preservative may also be employed to increase the shelf-life of the composition. A number of well-known and pharmaceutically acceptable preservatives may be used in the present composition, including, for example, parabens, thimerosal, chlorobutanol, benzalkonium chloride, or benzyl alcohol and combinations thereof. Other ingredients which extend shelf life can be added such as for example, antioxidants. Examples of antioxidants include sodium metabisulfite, potassium metabisulfite, ascorbyl palmitate and other pharmaceutically acceptable antioxidants. Typically, the antioxidant will be present in the composition in a concentration of from about 0.01% w/w to about 5% w/w.

Benzyl alcohol and benzalkonium chloride are preferred preservatives. A suitable concentration of preservative will depend on a number of factors, including, for example, the particular preservative selected, the intended shelf-life of the composition, and the results of preservative effectiveness and minimum preservative studies. When used, the concentration of the preservative in the composition will typically be from about 0.001% w/w to about 5% w/w, preferably from about 0.01% w/w to about 1% w/w and more preferably from about 0.02% w/w to about 0.4% w/w.

In one embodiment of the present invention, the cobalamin composition comprises sodium chloride, 0.649% w/w (0.11M); sodium phosphate, monobasic, anhydrous, 0.19% w/w (0.016M); benzyl alcohol, NF, 0.366% w/w (0.034M); sodium hydroxide, NF, 0.04% w/w (0.010M); benzalkonium chloride, 50%, NF, 0.02% w/w; cyanocobalamin, USP, 0.025% w/w (0.00018M); in purified water, USP, 98.71% w/w.

Alternatively, and in accordance with a preferred embodiment of the present invention, the cobalamin composition may be formulated to be a sterile, preservative-free composition. While preservatives may extend the shelf life of a composition, they may also cause or exacerbate irritation to the nasal membranes. Furthermore, because of the frequency with which the composition of the present invention is preferably administered, a bottle of typical volume for storing and dispensing the composition will likely be emptied by the patient before the occurrence of the degradation, spoilage, or bacterial growth that a preservative is meant to prevent.

Thus in another embodiment, the cobalamin composition is preservative-free and comprises sodium chloride, 0.649% w/w (0.11M); sodium phosphate, monobasic, anhydrous, 0.19% w/w (0.016M); sodium hydroxide, NF, 0.04% w/w (0.010M); cyanocobalamin, USP, 0.025% w/w (0.00018M); in purified water, USP, 99.096% w/w.

The composition may be prepared by methods known to those of skill in the art, including by combining or mixing the components according to generally accepted procedures. By way of example, the selected components may be simply mixed in a blender or other standard mixing machine to produce a concentrated composition which is then adjusted to the final concentration by the addition of water.

Typically, the cobalamin composition will be stored in and dispensed from a sealed container equipped with a metering valve and pump capable of being actuated to deliver or emit an aerosol (e.g., mist or spray) of the composition of predetermined volume into the patient's nostril and having a suitable droplet size distribution as known to those skilled in the art. Generally, the size of the droplets are large enough to prevent them from passing directly through the nasal passages and into the lungs, but small enough that they do not coalesce into large drops which either run out of the nose or down into the throat.

Suitable containers and metering valves for dispensing the cobalamin composition according to the methods of the invention are available commercially and are known to those of skill in the art. The container and valve system used to deliver the cobalamin composition may incorporate any of the conventional aerosol formation techniques. These include, for example, mechanical pumps; compressed air mechanisms in which delivery is made by hand pumping air into the container; compressed gas techniques in which delivery is made by the controlled release of a compressed gas (such as, for example, carbon dioxide, nitrogen, and dinitrogen oxide) into the cobalamin containing composition; and liquid propellant techniques in which a low boiling liquid hydrocarbon (such as, for example, butane, isobutane, propane, and other low boiling hydrocarbons in either pure or mixed forms), halohydrocarbon, fluorocarbons (such as, for example, FC-152A), chlorofluorocarbons (such as Freon or Freon like fluorocarbons, such as, for example, CFC-11, CFC-12 and CFC-114), and hydrofluorocarbons, also referred to as hydrofluoroalkanes (such as, for example, HFA-134a and HFA-227) are vaporized to exert a pressure and force the composition through the metering valve.

In accordance with a preferred embodiment, and especially when a preservative-free composition is formulated, the cobalamin composition is stored for administration in a container or bottle including a pump and metering valve adapted for delivery of a metered spray of the composition and designed to inhibit or prevent degradation or spoilage of and bacterial growth in the composition contained therein. Examples of such a container are the spray pump bottles produced by and available from Pfeiffer (Advanced Preservative Free System) and from Valois (VPY).

The following non-limiting example is provided to further illustrate the present invention. It should be appreciated by those skilled in the art that the techniques disclosed in the example that follows represent approaches the inventors have found function well in the practice of the invention, and thus can be considered to constitute examples of modes for its practice. However, those skilled in the art should, in light of the present disclosure, appreciate that many changes can be made in the specific embodiments that are disclosed and still obtain a like or similar result without departing from the spirit and scope of the invention.

EXAMPLE

The study comprised twenty-five subjects, ages 18-85, with a history of documented vitamin $B_{12}$ deficiency who had previously been receiving maintenance intramuscular (IM) injections of $B_{12}$. The purpose of this study was to determine whether as an alternative to IM injections, one daily administration of a 0.025% by weight cobalamin composition is sufficient to sustain an efficacious level of $B_{12}$ in place of IM therapy and, thereby, maintain a serum $B_{12}$ level within the therapeutic range of greater than about 200 ng/L.

As an alternative to an IM injection, an aqueous isotonic composition containing a cobalamin compound was provided to the subjects to allow them to dose themselves at home with one daily intranasal (IN) administration comprising two puffs or sprays of $B_{12}$ (cobalamin). The intranasal cobalamin composition used in this study is listed in Table 1.

TABLE 1

Cobalamin Containing Composition Used in Study

| Description | % w/w | Quantity Required per Batch | Molarity |
|---|---|---|---|
| Sodium Chloride | 0.649 | 248.1 gm | 0.11 |
| Sodium Phosphate, Monobasic, anhydrous | 0.19 | 72.6 gm | 0.016 |
| Benzyl Alcohol, NF | 0.366 | 139.9 gm | 0.034 |
| Sodium Hydroxide, NF | 0.04 | 15.3 gm | 0.010 |
| Benzalkonium Chloride, 50%, NF | 0.02 | 7.65 gm (3.83 g BAC + 3.83 g water) | NA (isomeric mix) |
| Cyanocobalamin, USP | 0.025 | 9.56 gm | 0.00018 |
| Purified Water, USP | 98.71 | 37.7 kg | NA |
| Total | 100 | 38.2 kg | NA |

Study Design

This study was an open label, non-randomized, single-arm, active treatment study. All subjects were instructed to complete daily diaries to record the date and time of administration and any adverse events.

Subjects with chronic $B_{12}$ deficiencies were treated with intramuscular (IM) injections every 4-8 weeks. At the midpoint of the usual IM therapy interval (between 2 and 4 weeks post injection) subjects presented at the clinic for screening and provided blood samples for the measurement of levels of vitamin $B_{12}$. At the end of the IM therapy interval (4 to 8 weeks post injection) the subjects returned to the clinic to provide a blood sample for a low level of $B_{12}$ measurement and began the intranasal 0.025% cyanocobalamin therapy. Each morning during the 8 week administration of nasal cyanocobalamin, subjects sprayed 1 spray (0.1 mL) of the saline solution containing 0.025% by weight cyanocobalamin from an upright metered dose bottle directly into each nostril for a 50 μg daily dose of cyanocobalamin.

Subjects returned to the clinic every two weeks (post dosing initiation) for eight weeks to provide blood samples for the evaluation of $B_{12}$ levels.

Primary Efficacy Analysis

The primary efficacy endpoint is the average of the vitamin $B_{12}$ levels from Visits 3, 4, 5 and 6 relative to the $B_{12}$ levels at Visit 1. The ratio of each post baseline value to baseline was calculated, and the repeated measures model was used to calculate the means of the ratios at each visit. The estimate statement (statement 1) provided an estimate of the average of the ratios across visits 3, 4, 5 and 6 and the confidence interval around that average.

Statistical Analysis

Because the study subjects are on different IM therapy intervals, Visit 1 and Visit 2 will not correspond to the same relative week. The following schedule describes the actual times:

Visit #1 (V1)—Midpoint between IM injections (anywhere from 2 to 4 weeks post IM therapy).

Visit #2 (V2)—Termination of IM therapy (anywhere from 4 to 8 weeks post IM therapy). This is the point at which the next IM injection would have been given, but for the fact that the study participants began intranasal therapy instead.

Visit #3 (V3)—2 weeks post IN therapy initiation.

Visit #4 (V4)—4 week post IN therapy initiation.
Visit #5 (V5)—6 weeks post IN therapy initiation.
Visit #6 (V6)—8 weeks post IN therapy initiation.
Analysis Results
Descriptive Statistics The average (standard deviation) age of the 25 subjects was 59.8 (15.5) years, ranging from 28.0 to 82.6 years. Seventeen (68.0%) of the subjects were female. Twenty-one (84.0%) were Caucasian and four (16.0%) were African American. The general pattern was an initial decline from Visit #1 to Visit #2 and a steady increase in the last four visits (Visits #3-#6), although there were exceptions. The mean $B_{12}$ value, range, and standard deviation at each visit are summarized in Table 2, and the means and their 95% confidence intervals are also shown in FIG. 1.

TABLE 2

SUMMARY OF $B_{12}$ LEVEL AT EACH VISIT DURING THE STUDY FOR THE 25 SUBJECTS

| Visit | N | Mean (pg/mL) | Standard Deviation (pg/mL) | Range (low-high) (pg/mL) |
|---|---|---|---|---|
| #1 | 25 | 484.28 | 157.93 | (419.09, 549.47) |
| #2 | 25 | 402.96 | 149.51 | (341.24, 464.68) |
| #3 | 25 | 505.76 | 136.73 | (449.32, 562.20) |
| #4 | 25 | 519.76 | 132.96 | (464.88, 574.64) |
| #5 | 25 | 510.60 | 162.41 | (443.56, 577.64) |
| #6 | 25 | 568.28 | 194.39 | (488.04, 648.52) |

The above description of the preferred embodiments is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

With reference to the use of the word(s) "comprise" or "comprises" or "comprising" in this specification, including the appended claims, unless the context requires otherwise, those words are used on the basis and clear understanding that they are to be interpreted inclusively, rather than exclusively, and that it is intended each of those words to be so interpreted in construing this specification.

What is claimed is:

1. A method for maintaining vitamin B12 blood serum levels in a subject, the method comprising intranasally administering to the subject in need thereof a composition such that a dose of from about 5 µg to about 45 µg of cyanocobalamin is administered, wherein the composition comprises an aqueous solution containing about 1% w/w cyanocobalamin, a pharmaceutically acceptable buffer, a humectant, and a preservative, and wherein:

the buffer comprises a citrate buffer;
the humectant comprises glycerin;
the preservative comprises benzalkonium chloride;
the composition has a pH of about 4 to about 6.5, and
the composition is provided in a container equipped with a pump adapted to deliver the composition into a patient's nostril.

2. The method according to claim 1, comprising administering the dose of cyanocobalamin in a plurality of metered sprays of the composition.

3. The method according to claim 1, comprising administering the dose of cyanocobalamin in a single metered spray of the composition.

4. The method of claim 1, wherein the composition is administered to provide a weekly dosage of from about 100 µg to about 1000 µg of cyanocobalamin.

5. The method of claim 1, wherein the composition is administered to provide a weekly dosage of from about 100 µg to about 800 µg of cyanocobalamin.

6. The method of claim 1, wherein the composition is administered to provide a weekly dosage of from about 100 µg to about 500 µg of cyanocobalamin.

7. The method of claim 1, wherein the dose is administered once daily.

8. A method for maintaining normal hematologic status in a pernicious anemia patient following intramuscular vitamin B12 injection therapy, said method comprising intranasally administering to the patient a composition such that a dose of from about 5 µg to about 45 µg of cyanocobalamin is administered, wherein the composition comprises an aqueous solution containing about 1% w/w cyanocobalamin, a pharmaceutically acceptable buffer, a humectant, and a preservative, and wherein:

the buffer comprises a citrate buffer;
the humectant comprises glycerin;
the preservative comprises benzalkonium chloride;
the composition has a pH of about 4 to about 6.5, and
the composition is provided in a container equipped with a pump adapted to deliver the composition into a patient's nostril.

9. The method according to claim 8, comprising administering the dose of cyanocobalamin in a plurality of metered sprays of the composition.

10. The method according to claim 8, comprising administering the dose of cyanocobalamin in a single metered spray of the composition.

11. The method of claim 8, wherein the composition is administered to provide a weekly dosage of from about 100 µg to about 1000 µg of cyanocobalamin.

12. The method of claim 8, wherein the composition is administered to provide a weekly dosage of from about 100 µg to about 800 µg of cyanocobalamin.

13. The method of claim 8, wherein the composition is administered to provide a weekly dosage of from about 100 µg to about 500 µg of cyanocobalamin.

* * * * *